(12) United States Patent
Moskovich et al.

(10) Patent No.: US 9,532,643 B2
(45) Date of Patent: Jan. 3, 2017

(54) ORAL CARE IMPLEMENT

(75) Inventors: Robert Moskovich, East Brunswick, NJ (US); Andreas Wechsler, Zell am See (AT); Michael Rooney, Millburn, NJ (US); Douglas Hohlbein, Hopewell, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 268 days.

(21) Appl. No.: 14/380,958

(22) PCT Filed: Mar. 1, 2012

(86) PCT No.: PCT/US2012/027167
§ 371 (c)(1),
(2), (4) Date: Aug. 26, 2014

(87) PCT Pub. No.: WO2013/130081
PCT Pub. Date: Sep. 6, 2013

(65) Prior Publication Data
US 2015/0000063 A1 Jan. 1, 2015

(51) Int. Cl.
*A46B 9/04* (2006.01)
*A46B 7/06* (2006.01)
(Continued)

(52) U.S. Cl.
CPC .............. *A46B 9/04* (2013.01); *A46B 5/0025* (2013.01); *A46B 7/06* (2013.01); *A46B 15/0081* (2013.01);
(Continued)

(58) Field of Classification Search
CPC ........... A46B 3/04; A46B 3/06; A46B 5/0025; A46B 5/0029; A46B 7/06; A46B 9/04; A46B 15/0075; A46B 15/0081; A46B 2200/1066; A61B 17/244; A61H 13/00
(Continued)

(56) References Cited

U.S. PATENT DOCUMENTS 2,263,802 A 5/1939 Grusin
3,398,421 A 3/1967 Rashbaum
(Continued)

FOREIGN PATENT DOCUMENTS

CN 2585581 11/2003
DE 20109123 U1 10/2002
(Continued)

OTHER PUBLICATIONS

International Search Report and the Written Opinion issued in International Application PCT/US2012/27167 mailed Jan. 17, 2013.
(Continued)

*Primary Examiner* — Mark Spisich

(57) ABSTRACT

An oral care implement having a head that achieves an enhanced cleaning action during brushing. In one embodiment, the invention can be an oral care implement comprising: a handle; a head connected to the handle and comprising a base structure (130) having a front surface (131), a rear surface (132), an island protruding from the rear surface of the base structure, and a passageway extending through the base structure from the front surface of the base structure to a rear surface of the island; a resilient soft tissue cleanser (170) on the rear surface of the base structure, the resilient soft tissue cleanser comprising an aperture through which the island extends; a mass (180) of a first resilient material positioned within the passageway so that a first portion (181) of the mass protrudes from the front surface of the head and a second portion (182) of the mass protrudes from the island, (Continued)

the island isolating the resilient soft tissue cleanser from the mass; and a plurality of teeth cleaning elements (105).

17 Claims, 8 Drawing Sheets

(51) Int. Cl.
  A61B 17/24 (2006.01)
  A46B 5/00 (2006.01)
  A46B 15/00 (2006.01)
(52) U.S. Cl.
  CPC ...... *A61B 17/244* (2013.01); *A46B 2200/1066* (2013.01)
(58) Field of Classification Search
  USPC ........ 15/110, 111, 167.1, 188, 201; 601/139, 601/141; 606/161
  See application file for complete search history.

(56) References Cited

U.S. PATENT DOCUMENTS

| | | |
|---|---|---|
| 5,524,319 A | 6/1996 | Avidor |
| 5,802,656 A | 9/1998 | Dawson et al. |
| 5,956,797 A | 9/1999 | Wilson |
| 6,931,688 B2 | 8/2005 | Moskovich et al. |
| 7,143,462 B2 | 12/2006 | Hohlbein |
| 7,480,955 B2 | 1/2009 | Hohlbein et al. |
| 7,614,111 B2 | 11/2009 | Moskovich et al. |
| 7,841,041 B2 | 11/2010 | Moskovich et al. |
| 2006/0195995 A1 | 9/2006 | Moskovich et al. |
| 2008/0086827 A1 | 4/2008 | Waguespack et al. |
| 2008/0147104 A1 | 6/2008 | Gatzemeyer et al. |
| 2009/0025165 A1 | 1/2009 | Moskovich et al. |
| 2010/0092916 A1 | 4/2010 | Teixeira et al. |
| 2011/0138563 A1 | 6/2011 | Phgura |
| 2011/0152909 A1 | 6/2011 | Jimenez et al. |
| 2011/0308026 A1 | 12/2011 | Jimenez et al. |

FOREIGN PATENT DOCUMENTS

| | | |
|---|---|---|
| DE | 202005009026 U1 | 11/2005 |
| DE | 102006025825 A1 | 12/2007 |
| EP | 1639913 | 3/2006 |
| WO | WO 97/32502 | 9/1997 |
| WO | WO 2007/051203 A1 | 5/2007 |
| WO | WO 2008/093300 A1 | 8/2008 |
| WO | WO 2008/103597 A1 | 8/2008 |
| WO | WO 2009/157932 A1 | 12/2009 |

OTHER PUBLICATIONS

Written Opinion of the International Preliminary Examining Authority issued in International Application PCT/US2012/27167 mailed Feb. 21, 2014.

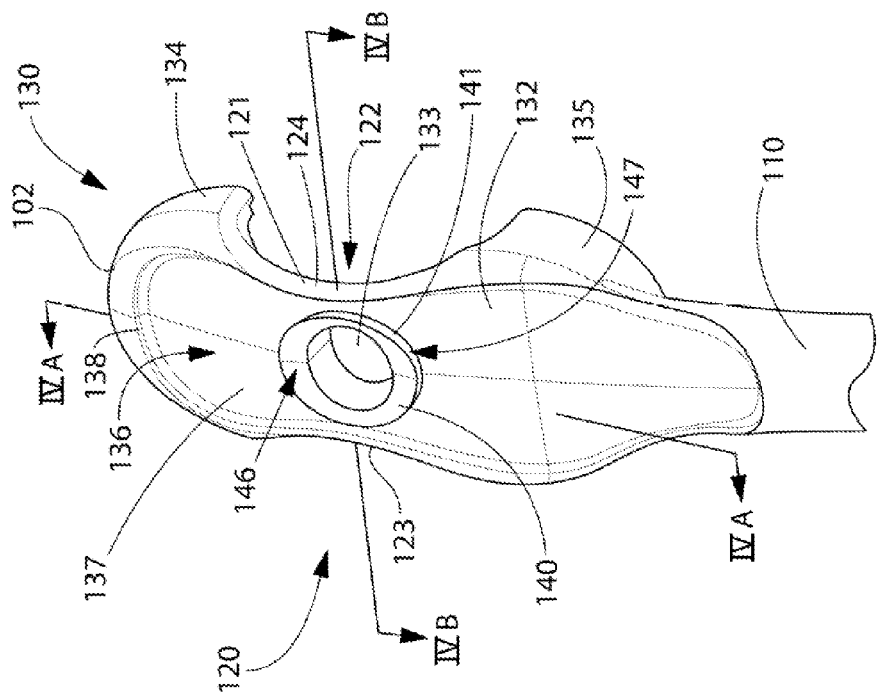
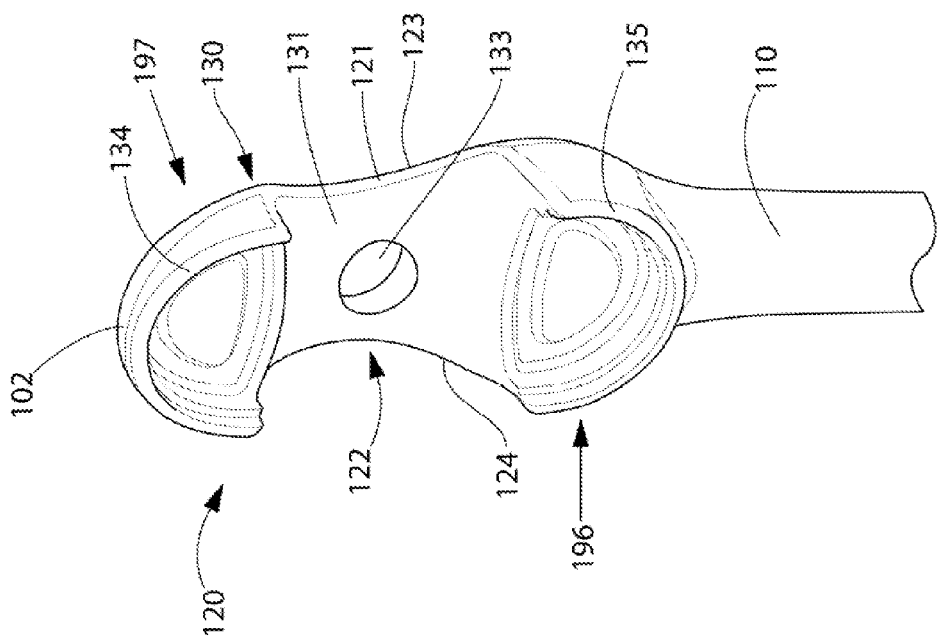

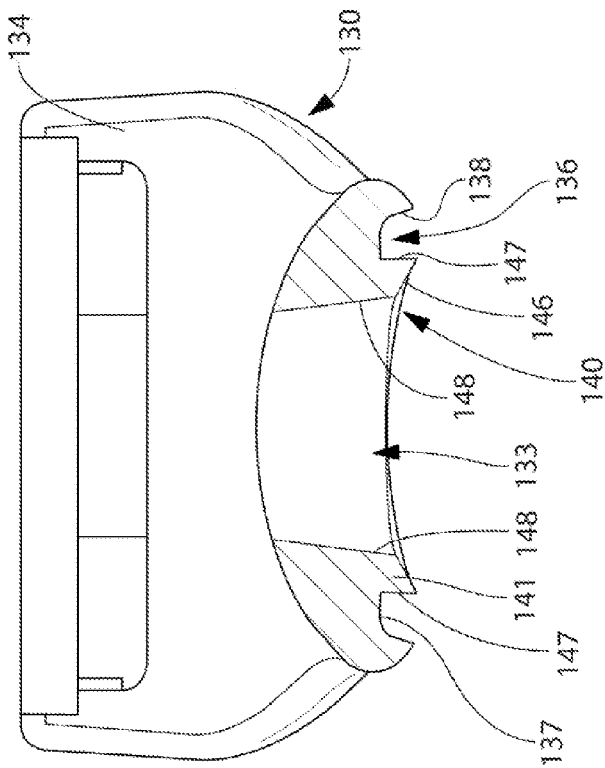
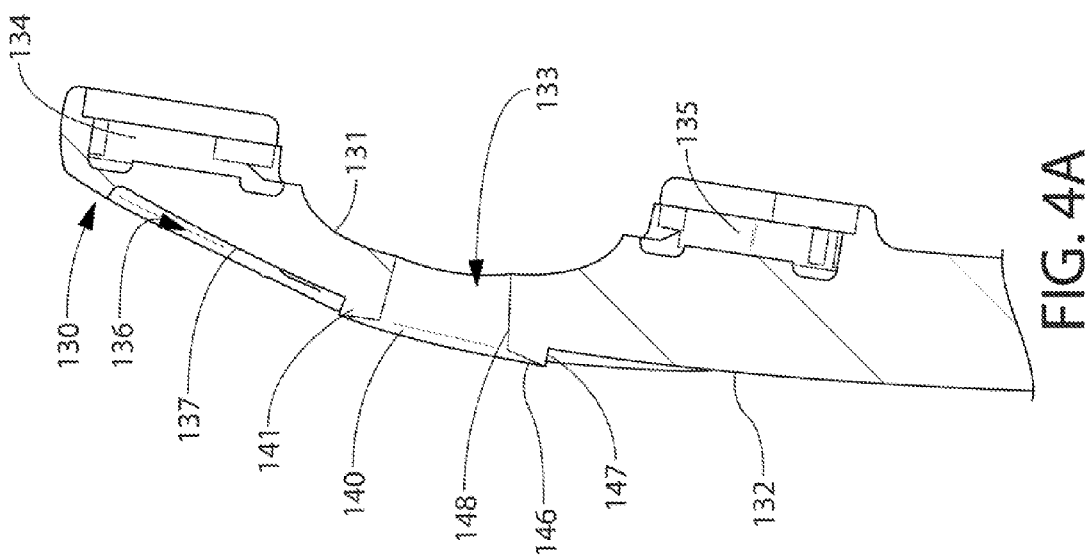
FIG. 4B
FIG. 4A

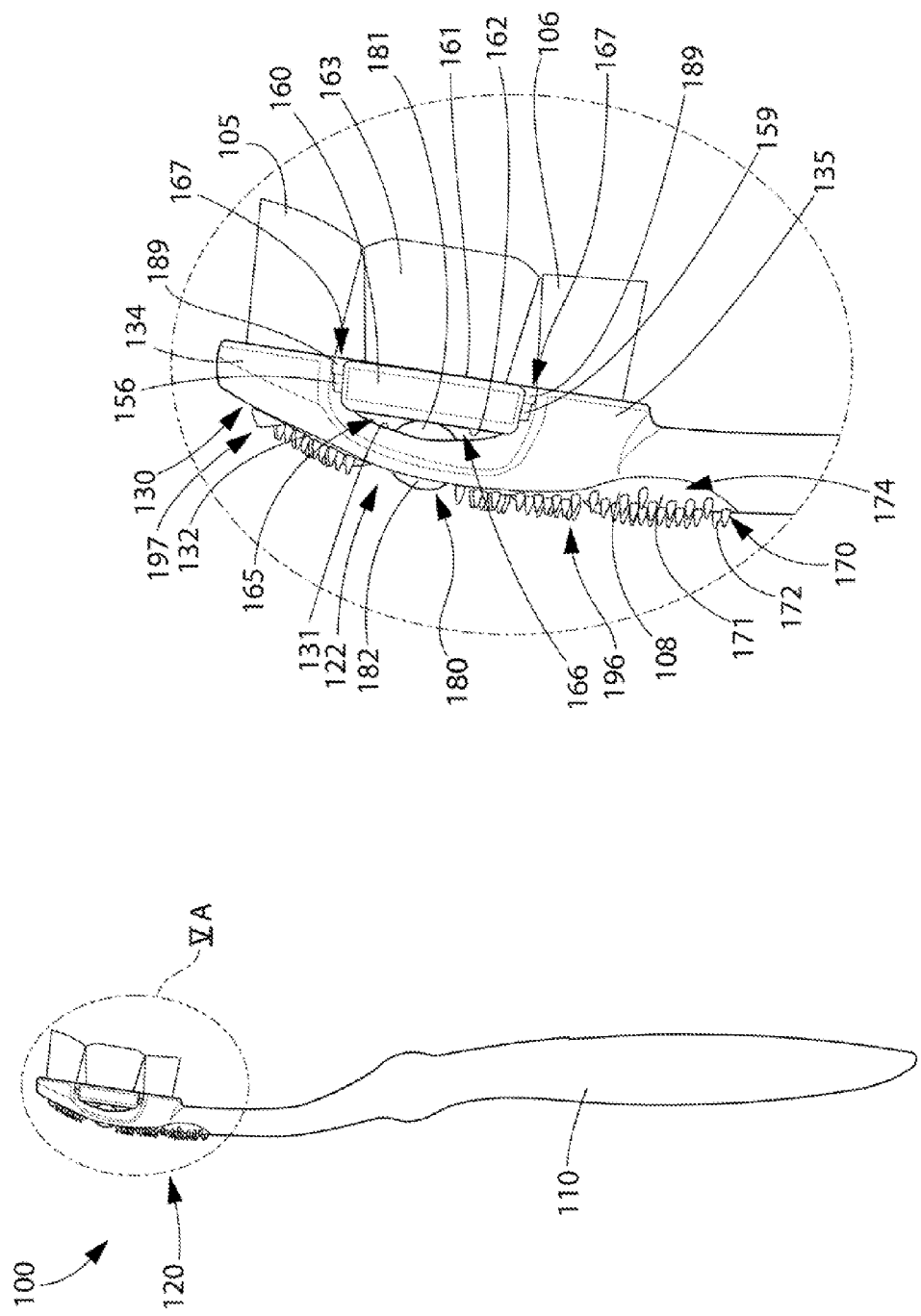

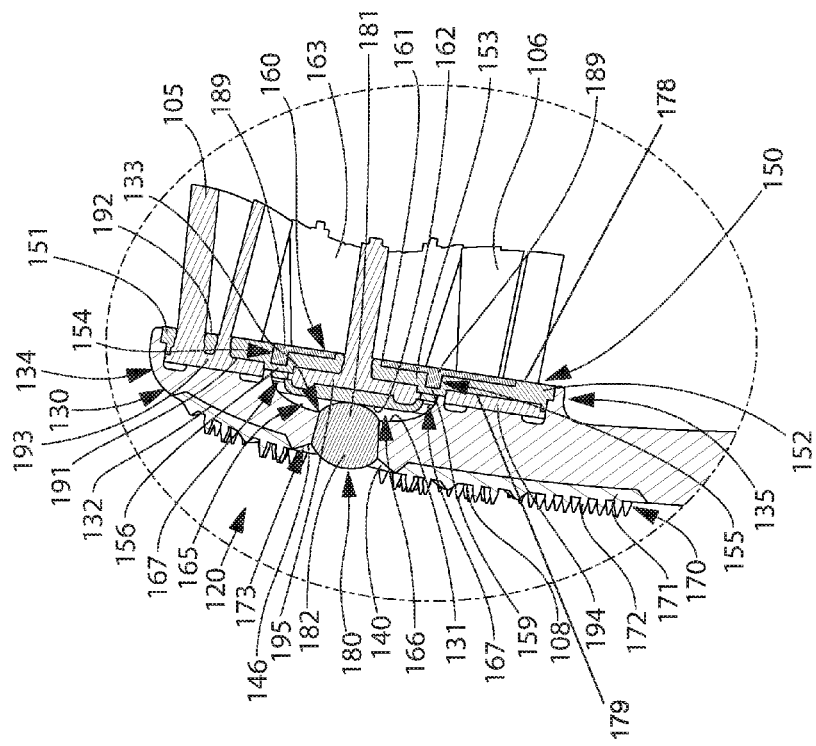
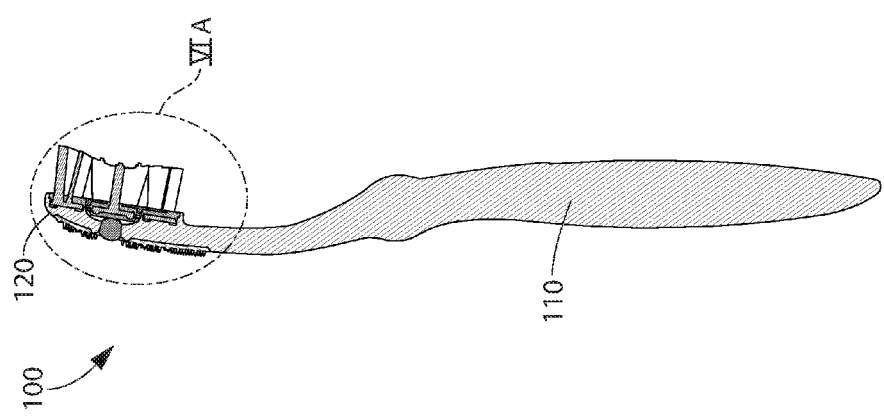
FIG. 6A
FIG. 6

ORAL CARE IMPLEMENT

CROSS-REFERENCE TO RELATED PATENT APPLICATIONS

The present application is a U.S. national stage entry under 35 U.S.C. §371 of Patent Cooperation Treaty Patent Application No. PCT/US2012/27167, filed Mar. 1, 2012, the entirety of which is incorporated herein by reference.

FIELD OF THE INVENTION

The present invention relates generally to oral care implements, and specifically to oral care implements, such as toothbrushes, having a head that achieves an enhanced cleaning action during brushing.

BACKGROUND OF THE INVENTION

A variety of toothbrush head configurations exist that have manually and/or mechanically-driven movable cleaning elements. Many of these configurations, however, include cleaning elements that extend from a rigid head. Teeth and gums by nature have a complex intricate contour. Due to the rigid nature of the attachment of the cleaning elements to the head of the toothbrush, the orientation of the cleaning elements is not flexible. Thus, a need exists for a toothbrush that achieves better flexibility of cleaning elements for an enhanced and improved cleaning action during brushing.

BRIEF SUMMARY OF THE INVENTION

The present invention is directed to an oral care implement. In one aspect, the oral care implement can include a handle and a head comprising a base structure. The base structure includes a front surface, a rear surface, a basin formed in the rear surface and an island protruding from the basin. A passageway extends through the base structure from the front surface of the base structure to the rear surface of the island. Furthermore, a mass of resilient material is positioned within the passageway and protrudes from the front surface of the base structure and from the island.

In one embodiment, the invention can be an oral care implement comprising: a handle; a head connected to the handle, the head comprising a base structure having a front surface, a rear surface, an island protruding from the rear surface of the base structure, and a passageway extending through the base structure from the front surface of the base structure to a rear surface of the island; a resilient soft tissue cleanser on the rear surface of the base structure, the resilient soft cleanser comprising an aperture through which the island extends; a mass of a first resilient material positioned within the passageway so that a first portion of the mass protrudes from the front surface of the head and a second portion of the mass is visible from the rear surface of the base structure, the island isolating the resilient soft tissue cleanser from the mass; and a plurality of teeth cleaning elements.

In a further embodiment, the invention can be an oral care implement comprising: an oral care implement comprising: a handle; a head connected to the handle, the head comprising a base structure having a front surface, a rear surface, a proximal portion, a distal portion, a narrowed waist portion between the proximal and distal portions, and a passageway located in the narrowed waist portion that extends through the base structure from the front surface of the base structure to a rear surface of the base structure; a carrier having a front surface and a rear surface, the carrier comprising a plurality of teeth cleaning elements extending from the front surface of the carrier, the carrier movably supported above the front surface of the base structure so that a gap exists between the rear surface of the carrier and the front surface of the base structure; a mass of a first resilient material positioned within the passageway so that a first portion of the mass protrudes from the front surface of the head into the gap and a second portion of the mass protrudes from the rear surface of the base structure; and wherein the first portion of the mass alters movement of the carrier relative to the head through contact with the rear surface of the carrier in response to a force being applied to the plurality of tooth cleaning elements of the carrier.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3A is a front perspective view of the base structure of the head of the oral care implement of FIG. 1;

FIG. 3B is a rear perspective view of the base structure of the head of the oral care implement of FIG. 1;

FIG. 4A is a cross-sectional view taken along line IVA-IVA of FIG. 3B;

FIG. 4B is a cross-sectional view taken along line IVB-IVB of FIG. 3B;

FIG. 5 is a side view of the oral care implement of FIG. 1;

FIG. 5A is a close-up view of area V-A of FIG. 5;

FIG. 6 is a cross-sectional view taken along line VI-VI of FIG. 1;

FIG. 6A is a close-up view of area VI-A of FIG. 6; and

DETAILED DESCRIPTION OF THE INVENTION

Figure 2:
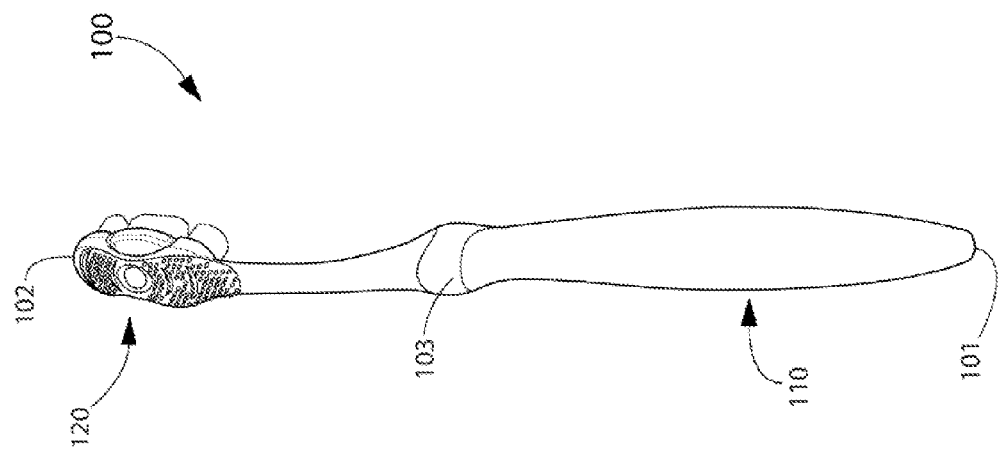
FIG. 2 is a rear perspective view of the oral care implement of FIG. 1.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Figure 1:
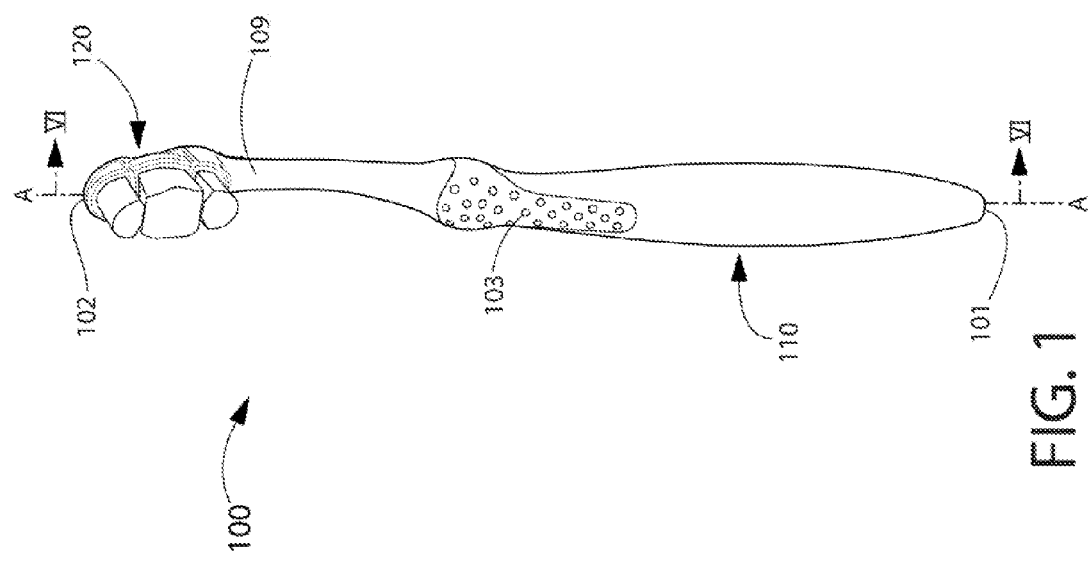
FIG. 1 is a front perspective view of an oral care implement in accordance with a first embodiment of the present invention.

Referring first to FIGS. 1 and 2 concurrently, an oral care implement 100 in accordance with an embodiment of the present invention will be described. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleaner, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement 100 extends along a longitudinal axis A-A from a proximal end 101 to a distal end 102. The oral care implement 100 generally comprises a handle 110 and a head 120. The handle 110 is an elongated structure that provides the mechanism by which the user can hold and manipulate the oral care implement 100 during use. The handle 110 can take on a wide variety of shapes, contours and configurations, none of which are limiting of the present invention. In the exemplified embodiment, the handle 110 is formed of a rigid material, such as a hard plastic material. The hard plastic material that can be used to form the handle 110 includes, for example without limitation, polypropylene, polymers and copolymers of ethylene, propylene, butadiene, vinyl compounds and polyesters such as polyethylene terephthalate. Of course, the invention is not to be so limited in all embodiments and the handle 110 may be formed with a resilient material, such as a thermoplastic elastomer, over portions of or the entirety of the handle 110 to enhance the gripability of the handle 110 during use. In the exemplified embodiment, the handle 110 comprises a resilient material 103 in the thumb grip region. Thus, the resilient material 103 is in the region of the handle 110 that will be gripped by a user's thumb and forefinger during use of the oral care implement 100.

The head 120 is coupled to a distal end 109 of the handle 110. In the exemplified embodiment, the head 120 and the handle 110 are integrally formed as a single unitary structure using a molding, milling, machining or other suitable process. However, in other embodiments the handle 110 and the head 120 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 120 and the handle 110 are of a unitary or multi-piece construction (including connection techniques) is not limiting of the present invention unless specifically claimed. In some embodiments of the invention, the head 120 may be detachable (and replaceable) from the handle 110 using techniques known in the art.

Figure 3C:
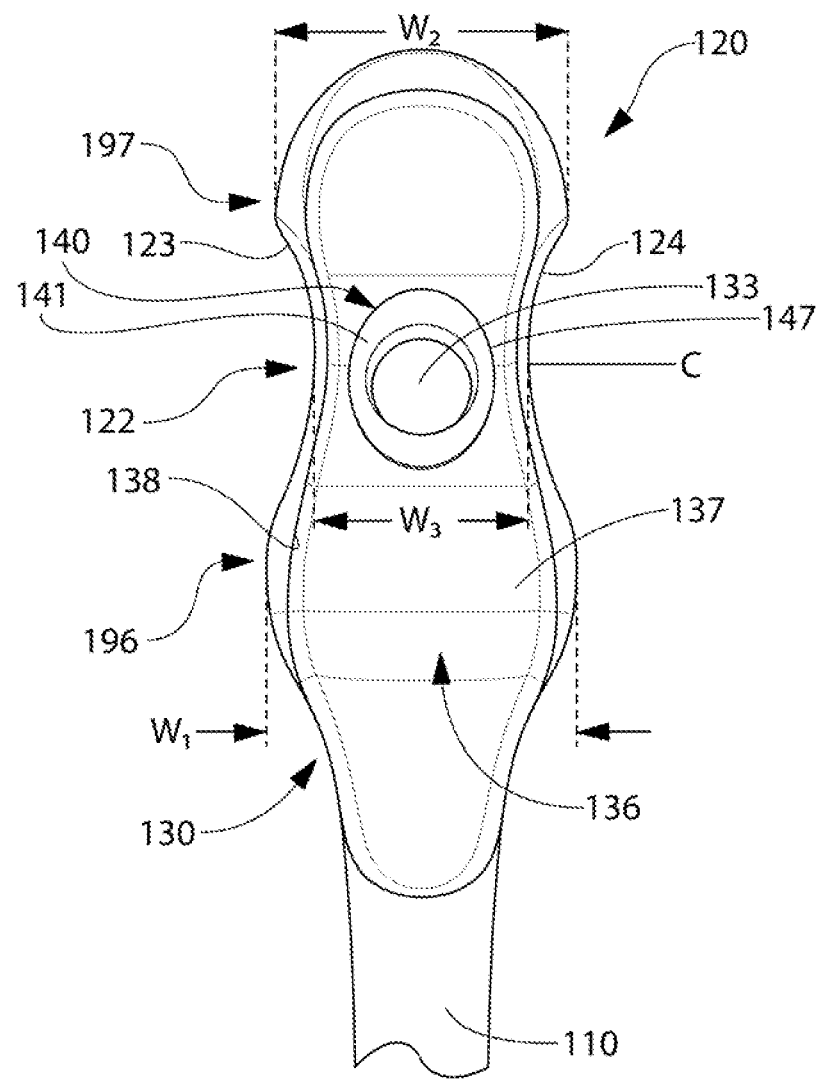
FIG. 3C is a rear view of the base structure of the head of the oral care implement of FIG. 1.

Referring to FIGS. 3A-3C concurrently, the head 120 will be described in more detail. The head 120 of the oral care implement 100 generally comprises a base structure 130 having a front surface 131, an opposing rear surface 132 and a passageway 133 extending through the base structure 130 from the front surface 131 to the rear surface 132. In certain other embodiments, the passageway 133 may not extend entirely through the base structure 130 and may merely form an opening in the front surface 131 of the base structure 130 such that the opening forms a socket in the front surface 131 of the base structure 130 rather than a passageway through the base structure 130. In still other embodiments the passageway 133 may merely form an opening in the rear surface 132 of the base structure 130 such that the opening forms a socket in the rear surface 132 of the base structure 130 rather than a passageway through the base structure 130.

The base structure 130 comprises a proximal portion 196, a distal portion 197 and a narrowed waist portion 122 longitudinally positioned in between the proximal and distal portions 196, 197. Due to the narrowed waist portion 122, the base structure 130 is in the general shape of an hourglass in that it is wider at the top and bottom and narrower in the middle. In the exemplified embodiment, the base structure 130 comprises a first pod 134 extending from the front surface 131 of the base structure 130 at the distal portion 197 of the base structure 130 (which is also the distal end 102 of the oral care implement 100) and a second pod 135 extending from the front surface 131 of the base structure 130 at the proximal portion 196 of the base structure 130. The terms first pod 134 and second pod 135, as used herein, differentiate between different pods of the oral care implement 100 without any specific location on the head being implied. Thus, in certain embodiments the first pod 134 can be positioned at the proximal portion 196 of the base structure 130 and the second pod 135 can be positioned at the distal portion 197 of the base structure 130.

Moreover, although the components extending from the front surface 131 of the base structure 130 at the proximal and distal portions 196, 197 of the base structure 130 are referred to herein as first and second pods 134, 135, the invention is not to be so limited in all embodiments. Thus, in certain embodiments each of the first and second pods 134, 135 can be a protuberance extending upwardly from the front surface 131 of the base structure 130, such as an upstanding wall, a hinge, a strut or the like. In such embodiments, the first pod 134 may be referred to herein as a first protuberance and the second pod 135 may be referred to herein as a second protuberance. The first and second pods 134, 135 are not limited to having a rounded or semi-rounded shape but may be any shaped member extending from the front surface 131 of the base structure 130. Furthermore, although the invention is illustrated and described herein as having the first pod 134 and the second pod 135, in certain embodiments the invention may comprise only one of the pods or only a single protuberance extending upwardly from the front surface 131 of the base structure 130.

The base structure 130 comprises a generally U-shaped cross-section extending longitudinally from the first pod 134 to the second pod 135. The U-shaped cross-section is formed by the first and second pods 134, 135 extending upwardly from the front surface 131 of the base structure 130 at the proximal and distal portions 196, 197 of the base structure 130, respectively. The portion of the base structure 130 that is longitudinally positioned in between the first and second pods 134, 135 (i.e., the narrowed waist portion 122) does not have any component extending upward from the front surface 131 of the base structure 130, and thereby forms the bottom curved portion of the U-shape of the base structure 130. This shape of the base structure 130 facilitates movably mounting cleaning elements to the base structure 130 as will be described in more detail below.

Each of the first and second pods 134, 135 are formed integrally with and form a part of the base structure 130. Furthermore, the base structure 130 is formed from a rigid material such as a hard plastic (i.e., any of the hard plastic materials listed above with regard to the handle 110). Due to the integral formation of the first and second pods 134, 135 with the base structure 130, each of the first and second pods 134, 135 are substantially non-movable with respect to the base structure 130. Thus, although there is inherent flexibility in all materials, the first and second pods 134, 135 are substantially unable to move relative to the base structure 130 due to their hard plastic material and integral formation.

The base structure 130 of the head 120 of the oral care implement 100 comprises a peripheral sidewall 121 that extends between the front and rear surfaces 131, 132 of the base structure 130. The peripheral sidewall 121 forms the periphery of the base structure 130. The peripheral sidewall 121 includes a first side wall 123 and an opposing second side wall 124. Each of the first and second side walls 123, 124 of the peripheral sidewall 121 is contoured so as to form the periphery of the proximal and distal portions 196, 197 as well as the waist portion 122 and to give the base structure 130 the hourglass shape noted above.

The first side wall 123 forms a first concave edge in the region of the waist portion 122 of the base structure 130 and the second side wall 124 forms a second concave edge in the region of the waist portion 122 of the base structure. Thus, the waist portion 122 is a narrowed portion of the base structure 130 positioned longitudinally between the proximal and distal portions 196, 197 of the base structure 130 (and hence also between the first and second pods 134, 135). Of course, the invention is not to be particularly limited by the contours and shapes of the base structure 130 in all embodiments unless so specified in the claims.

As noted above, the base structure 130 extends from the proximal portion 196 to the distal portion 197. The base structure 130 has a first width $W_1$ at the widest point of the proximal portion 196 and a second width $W_2$ at the widest point of the distal portion 197. In the exemplified embodiment, the first width $W_1$ is substantially the same as the second width $W_2$. However, the invention is not to be so limited in all embodiments and in certain other embodiments the first width $W_1$ can be greater than the second width $W_2$ or vice versa.

The width of the base structure 130 gradually decreases as the base structure 130 extends from the proximal portion 196 to a longitudinal center C of the base portion 130. The width of the base structure 130 then gradually increases as the base structure 130 extends from the longitudinal center C to the distal portion 197. As a result of the gradual increasing and decreasing of the width from the proximal portion 196 to the distal portion 197, the narrowed waist portion 122 of the base structure 130 has a varied width. Furthermore, each of the first and second side walls 123, 124 forms a concave edge in the region of the narrowed waist portion 122 (i.e., between the proximal and distal portions 196, 197 of the base structure 130). The waist portion 122 has a third width $W_3$ at the longitudinal center C. The third width $W_3$ is less than each of the first and second widths $W_1$, $W_2$ and is the narrowest portion of the narrowed waist portion 122 of the base structure 130. In certain embodiments, the third width $W_3$ is between 60% and 80% of the first and second widths $W_1$, $W_2$, and more specifically between 65% and 80% of the first and second widths $W_1$, $W_2$.

Although the base structure 130 is described herein as having its narrowest portion at the longitudinal center C of the base structure 130, the longitudinal center C is not the actual center of the base structure 130 in all embodiments. Rather, the longitudinal center C is the point on the base structure 130 that is the narrowest within the narrowed waist portion 122. Thus, although the narrowed waist portion 122 of the base structure 130 is positioned longitudinally between the proximal and distal portions 196, 197 of the base structure 130, the narrowed waist portion 122 is not centered longitudinally along the base structure 130 in all embodiments.

The rear surface 132 of the base structure 130 comprises a basin 136 having a floor 137. In certain embodiments, the floor 137 can be conceptually considered as a part of the rear surface 132 of the base structure 130. The basin 136 is defined by an upstanding wall 138 that extends upwardly from the floor 137 and surrounds the basin 136. The upstanding wall 138 forms a peripheral sidewall of the basin 138.

The base structure 130 further comprises an island 140 extending from the floor 137 of the basin 136. The island 140 is formed by an annular wall 141 extending upwardly from the floor 137 of the basin 136. The island 140, and more specifically the annular wall 141 of the island 140, comprises an outer sidewall surface 147 extending upwardly from the floor 137 of the basin 136. In the exemplified embodiment, the island 140 is located in the narrowed waist portion 122 of the base structure 130. Furthermore, the passageway 133 is located within the island 140, and specifically extends through the base structure 130 from the front surface 131 of the base structure 130 to a rear surface 146 of the island 140. Thus, the island 140 is an annular, ring-like structure with the passageway 133 centrally formed into the island 140. The invention is not to be limited to the island 140 being located in the narrowed waist portion 122 of the base structure 130 in all embodiments and in certain other embodiments the location of the island 140, and hence also the passageway 133, can be modified.

As noted above, in the exemplified embodiment the base structure 130 of the head 120 is formed integrally with the handle 110. Furthermore, the island 140 is also integrally formed with the base structure 130. Thus, in the exemplified embodiment the base structure 130 (including the island 140) and the handle 110 are a single, unitary component formed of a rigid plastic material, such as polymers and copolymers of ethylene, propylene, butadiene, vinyl compounds and polyesters such as polyethylene terephthalate. The preferred material for the handle 110 is polypropylene. However, as noted above in other embodiments the head 120, and hence the base structure 130 and island 140, can be separately formed from the handle 110 and later attached thereto. However, regardless of whether the base structure 130 and handle 110 are integrally or separately formed, the island 140 forms a part of and is integrally formed with the base structure 130.

Referring to FIGS. 4A and 4B concurrently, the oral care implement 100 will be described in more detail. FIGS. 4A and 4B illustrate the general contours and shapes of the island 140 and the passageway 133. As can be seen, the island 140 is formed by the annular wall 141 that protrudes from the floor 137 of the basin 136. The island 140 has an outer sidewall surface 147 that is spaced from the upstanding wall 138 that defines the periphery of the basin 136.

In the exemplified embodiment, the rear surface 146 of the island 140, which forms the free end of the island 140 as it extends from the floor 137 of the basin 136, is concave. Thus, the rear surface 146 of the island 140 extends further from the floor 137 of the basin 136 at the outer sidewall surface 147 than at an inner sidewall surface 148 that substantially surrounds and defines the passageway 133. Thus, the rear surface 146 of the island 140 angles inwardly towards the floor 137 of the basin 138 as it extends from the outer sidewall surface 147 to the inner sidewall surface 148.

As noted above, the passageway 133 is defined by the inner sidewall surface 148 of the island 140. In the exemplified embodiment, the inner sidewall surface 148 of the island 140 converges as it extends from the rear surface 146 of the island 140 towards the front surface 131 of the base structure 130. Thus, the passageway 133 has a cross-sectional area that tapers from the rear surface 146 of the island 140 to the front surface 131 of the base structure 130. Of course, the invention is not to be so limited in all embodiments and in certain other embodiments the passageway 133 may have a constant cross-sectional area or a cross-sectional area that tapers from the front surface 131 of the base structure 130 to the rear surface 146 of the island 140.

Referring to FIGS. 5-6A concurrently, the oral care implement will be further described. The oral care implement 100 comprises a carrier 160 having a front surface 161 and a rear surface 162. The carrier 160 comprises a plurality of tooth cleaning elements 163, which extend from the front surface 161 of the carrier 160. As will be described in more detail below, in certain embodiments a portion of the carrier 160 is formed by a head plate and the tooth cleaning elements 163 are connected to the head plate via an anchor free tufting technique.

The carrier 160 is not directly connected to the base structure 130 of the head 120. Rather, the carrier 160 is supported above the front surface 131 of the base structure 130 such that a gap 165 exists between the rear surface 162 of the carrier 160 and the front surface 131 of the base structure 130. As will be described in detail below, the carrier 160 is supported above the front surface 131 of the base structure 130 in a manner that enables the carrier 160 to be movable in various directions. Thus, the carrier 160 is movably supported above the front surface 131 of the base structure 130. The gap 165 forms a transverse passageway 166 from the first side surface 123 of the base structure 130 of the head 120 to the second side surface 124 of the base structure 130 of the head 120.

In the exemplified embodiment, the carrier 160 is positioned between the first pod 134 and the second pod 135 and is supported above the narrowed waist portion 122 of the base structure 130. However, as noted above one of the first or second pods 134, 135 may be omitted in other embodiments such that the carrier 160 is positioned adjacent to only one of the pods 134, 135 and supported thereby in a cantilever manner (FIG. 8). Regardless, the carrier 160 is supported above the first surface 131 of the base structure 130 by at least the first pod 134. In the exemplified embodiment, the carrier 160 is supported above the first surface 131 of the base structure 130 by both the first and second pods 134, 135. Specifically, the carrier 160 is supported above the front surface 131 of the base structure 140 by resilient connections 167 to each of the first and second pods 134, 135 such that the carrier 160 is movable relative to the head 120 and base structure 130 (and relative to the first and second pods 134, 135). The structure that facilitates the resilient connections 167 between the carrier 160 and each of the first and second pods 134, 135 will be described in more detail below with specific reference to FIGS. 6-7.

In addition to the carrier 160 comprising tooth cleaning elements 163 extending therefrom, the first pod 134 comprises a plurality of tooth cleaning elements 105 extending therefrom and the second pod 135 comprises a plurality of tooth cleaning elements 106 extending therefrom. Attachment of the tooth cleaning elements 105, 106 to the first and second pods 134, 135 is achieved via an anchor free tufting technique and will be described in more detail below with reference to FIGS. 6-7.

As discussed above, the rear surface 132 of the base structure 130 comprises the basin 136 formed therein. Furthermore, in the exemplified embodiment the rear surface 132 of the base structure 130 comprises a resilient soft tissue cleanser 170. The soft tissue cleanser 170 comprises a pad portion 171 and a plurality of protuberances 172 protruding from the pad portion 171. The pad portion 171 of the soft tissue cleanser 170 is disposed in the basin 136 and an outer surface 174 of the pad portion 171 of the soft tissue cleanser 170 is flush with the rear surface 132 of the base structure 130 of the head 120. Thus, the tissue cleanser 170 forms a portion of the outer surface of the head 120 of the oral care implement 100. The pad portion 171 of the soft tissue cleanser 170 further includes an aperture 173 that surrounds the annular wall 141 that forms the island 140. Thus, the island 140 extends through the aperture 173 of the pad portion 171 of the soft tissue cleanser 170.

The outer sidewall surface 147 of the island 140 is circumferentially surrounded by the resilient soft tissue cleanser 170. In certain embodiments, the resilient soft tissue cleanser 170 abuts against the outer sidewall surface 147 of the island 140, although the invention is not to be so limited in all embodiments and in certain other embodiments a space may exist between the resilient soft tissue cleanser 170 and the outer sidewall surface 147 of the island 140. Thus, the soft tissue cleanser 170 is separated and/or isolated from the passageway 133 by the island 140. In certain embodiments, the soft tissue cleanser 170 is formed into the basin 136 via an injection molding technique.

In the exemplified embodiment, each of the plurality of protuberances 172 is in the form of a nub. As used herein a "nub" generally refers to a column-like protrusion (without limitation to the cross-sectional shape of the protrusion) which is upstanding from a base surface. In a general sense, the protuberances 172 in the preferred construction have a height that is greater than the width at the base of the protuberance 172 (as measured in the longest direction). Nevertheless, protuberances or nubs could include projections wherein the widths and heights are roughly the same or wherein the heights are somewhat smaller than the base widths. Moreover, in some circumstances (e.g., where the protuberances tapers to a tip or includes a base portion that narrows to a smaller projection), the base width can be substantially larger than the height.

In one preferred arrangement of the soft tissue cleanser 170, the plurality of protuberances 172 are conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections. In the exemplified embodiment, the soft tissue cleanser 170 including the pad 171 and the protuberances 172 are formed from a resilient material, such as an injection molded thermoplastic elastomer. An example of a suitable elastomeric soft tissue cleaner that may be used with the present invention and positioned on the rear surface 132 of the base structure 130 of the head 120 is disclosed in U.S. Pat. No. 7,143,462, issued Dec. 5, 2006 to the assignee of the present application, the entirety of which is hereby incorporated by reference. In certain other embodiments, the protuberances 172 of the soft tissue cleanser 170 can take the form of elongated ridges, nubs, or combinations thereof.

Still referring to FIGS. 5-6A, as discussed above the base structure 130 comprises a passageway 133 from the rear surface 132 of the base structure 130 (and more specifically from the rear surface 146 of the island 140) to the front surface 131 of the base structure 130. In the exemplified embodiment, a mass 180 formed of a first resilient material is positioned within the passageway 133. A first portion 181 of the mass 180 protrudes from the front surface 131 of the base structure 130 of the head 120 and into the gap 165 between the rear surface 162 of the carrier 160 and the front surface 131 of the base structure 130. A second portion 182 of the mass 180 is visible from the rear surface 132 and also protrudes from the rear surface 132 of the base structure 130. In some embodiments, the second portion 182 of the mass 180 doesn't protrude from the rear surface 132, but it is visible from the rear surface 132. In embodiments that comprise the island 140 on the rear surface 132 of the base structure 130, the second portion 182 of the mass 180 protrudes from the island 140. Furthermore, in certain embodiments the second portion 182 of the mass 180 also protrudes from a rear surface 108 of the head 120 that is formed by the outer surface 174 of the pad 171 of the soft tissue cleanser 170 from which the protuberances 172 protrude.

As noted above, the mass 180 comprises a first resilient material. In the exemplified embodiment, the mass 180 is entirely formed from the resilient material. Suitable resilient materials for forming the mass 180 include injection molded thermoplastic elastomer or other rubber materials that are capable of resilient deformation and/or displacement. However, the invention is not to be so limited in all embodiments and the mass 180 can be formed of other resilient materials in certain other embodiments. Furthermore, although the mass 180 is illustrated being formed entirely of the resilient material, in certain other embodiments the mass 180 may comprise a core that is formed of a rigid material, such as any of the hard plastic materials described herein, and a shell or overmold layer formed of the resilient material. In still other embodiments, the first portion 181 of the mass 180 can be formed of a resilient material while the second portion 182 of the mass 180 is formed of a rigid material. Other embodiments of the spheroid that achieve the functionality described below are contemplated. Thus, the mass 180 is not limited to being formed entirely of a resilient material in all embodiments.

Furthermore, in the exemplified embodiment the mass 180 is illustrated being substantially spherical in shape. However, the invention is not to be so limited in all embodiments and in certain other embodiments the mass 180 may take on other spheroid-type shapes, such as for example without limitation an oblate spheroid, a prolate spheroid, an ellipsoid, an ovoid or any par- or truncated versions thereof. Thus, shapes other than those exemplified are contemplated for the mass 180 of the present invention and the mass 180 is not to be particularly limited by its shape in all embodiments unless so specified in the claims.

As noted above, the mass 180 has a first portion 181 that protrudes from the front surface 131 of the base structure 130 into the gap 165 and a second portion 182 that protrudes from the rear surface 132 of the base structure 130, and more specifically from the rear surface 146 of the island 140. Furthermore, the first portion 181 of the mass 180 comprises a first domed surface and the second portion 182 of the mass 180 comprises a second domed surface. Thus, each of the first and second portions 181, 182 of the mass 180 protrude from their respective surfaces so as to form a dome-shaped surface.

In the exemplified embodiment, the first portion 181 of the mass 180 that protrudes from the front surface 131 of the base structure 130 and into the gap 165 is in surface contact with the rear surface 162 of the carrier 160. Of course, the invention is not to be so limited in all embodiments and in certain other embodiments the first portion 181 of the mass 180 may protrude into the gap 165 without contacting the rear surface 161 of the carrier 160.

The mass 180 alters movement of the carrier 160 relative to the base structure 130 of the head 120 through surface contact with the rear surface 162 of the carrier 160. Specifically, due to being formed at least partially of a resilient material, the mass 180 is deformable and/or displaceable within the passageway 133 and/or within the gap 165. Thus, during brushing as brushing forces are applied to the plurality of tooth cleaning elements 163 extending from the carrier 160, the carrier 160 translates downwardly in a direction toward the front surface 131 of the base structure 130 by such deformation and/or displacement of the mass 180 relative to the base structure 130. The resilient connection 167 between the carrier 160 and the first and/or second pods 134, 135 facilitates such translational movement of the carrier 160 in response to a brushing force being applied to the carrier 160 in the direction of the front surface 131 of the base structure 130. The force imparted onto the carrier 160 during brushing is sufficient to deform or displace the mass 180 to create such a translational movement of the carrier 160 relative to the base structure 130.

Furthermore, due to its shape, and specifically the shape of the first domed surface of the first portion 181 of the mass 180, the mass 180 acts as a pivot on which the carrier 160 can move. Thus, the carrier 160 can pivot with respect to the base structure 130 about the first portion 181 of the mass 180. The direction of pivot of the carrier 160 is in a side-to-side direction transverse to the longitudinal axis A-A. As will be described in more detail below, the resilient connection 167 between the carrier 160 and the first and/or second pods 134, 135 also facilitates the pivoting and translational movements of the carrier 160 relative to the base structure 130.

As described above, the carrier 160 is supported above the front surface 131 of the base structure 130 so as to be positioned above the narrowed waist portion 122 of the base structure 130. The narrowed waist portion 122 of the base structure 130 increases the permissible degree of the pivoting motion of the carrier 160. If the narrowed waist portion 122 were omitted and the first and second sidewalls 123, 124 of the base structure 130 below the carrier 160 were not narrowed as described herein, side-to-side movement of the carrier 160 relative to the base structure 130 would be restricted because the carrier 160 would come into contact with the first and second sidewalls 123, 124 during such pivoting. By narrowing the sidewalls 123, 124 in the base structure 130 in a location that is below the carrier 160, side-to-side pivoting motion of the carrier 160 is less restricted than it would otherwise be.

In certain embodiments, both the soft tissue cleanser 170 and the mass 180 are formed into or connected to the head 120 via an injection molding step. However, as noted above the soft tissue cleanser 170 is separated or isolated from the passageway 133 by the island 140, and more specifically by the outer sidewall surface 147 of the island 140. Furthermore, as noted above the mass 180 is positioned within the passageway 133. Thus, the soft tissue cleanser 170 is also isolated from the mass 180 by the island 140 (and specifically by the annular wall 141 of the island 140). Although the mass 180 and the soft tissue cleanser 170 are both formed from an injection molding technique, each is made from a separate injection molding shot. The mass 180 and soft tissue cleanser 170 are not unitary or integral, but rather are separate components that are both isolated from one another and separately formed from one another. Furthermore, the soft tissue cleanser 170 and the mass 180 may be formed of different materials, such that the mass 180 has a greater Shore durometer (e.g., Shore A hardness value) than the soft tissue cleanser 170 or vice versa. In certain embodiments the mass 180 is formed of or comprises a first resilient material and the soft tissue cleanser 170 is formed of or comprises a second resilient material. In certain embodiments the second resilient material is the same as the first resilient material and in other embodiments the second resilient material is different from the first resilient material.

Figure 7:
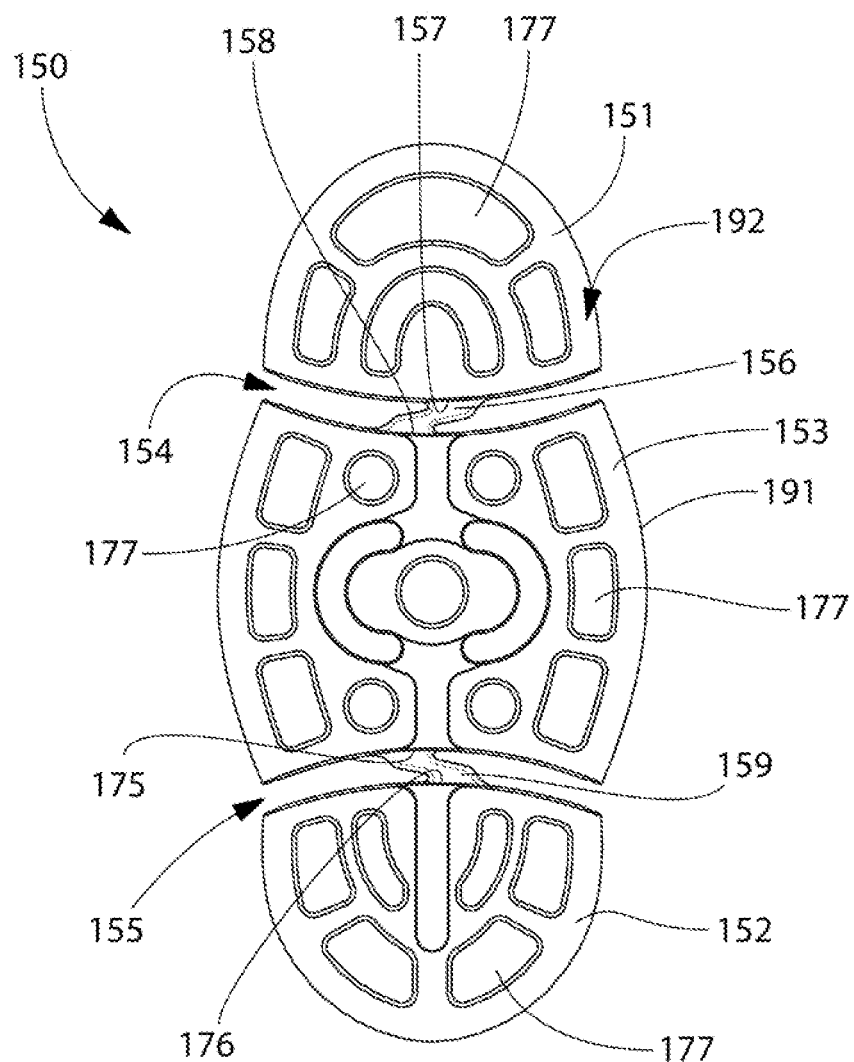
FIG. 7 is a front view of the head plate of the oral care implement of FIG. 1 with the resilient material omitted.
Figure 8:
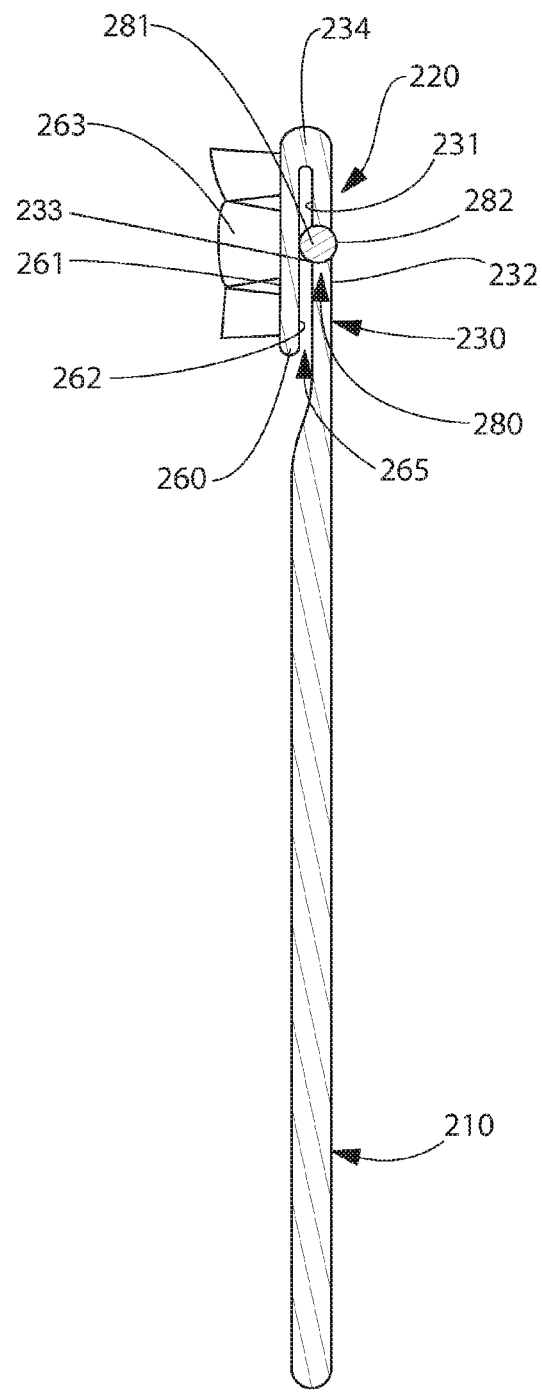
FIG. 8 is a longitudinal cross-sectional view of an oral care implement in accordance with a second embodiment of the present invention.

Referring to FIGS. 6-7 concurrently, a unitary head plate 150 of the oral care implement 100 will be described. As will be described in more detail below, the head plate 150 is used for mounting the tooth cleaning elements via an anchor free tufting technique. After the tooth cleaning elements are mounted to the head plate 150, the head plate 150 is secured to the base structure 130 of the head 120 such as by ultrasonic welding. Of course, the head plate 150 can be secured to the base structure 130 of the head 120 by techniques other than ultrasonic welding, such as for example without limitation thermal welding, a tight-fit assembly, a coupling sleeve, threaded engagement, adhesion, fasteners, a snap-fit or the like.

The unitary head plate 150 generally comprises a first end portion 151, a second end portion 152 and a middle portion 153. A first transverse channel 154 extends between the first end portion 151 and the middle portion 153 forming a gap therebetween. A second transverse channel 155 extends between the second end portion 152 and the middle portion 153 forming a gap therebetween. Furthermore, a first strut 156 extends longitudinally through the first transverse channel 154 from a proximal end 157 of the first end portion 151 to a distal end 158 of the middle portion 153 to connect the first end portion 151 to the middle portion 153. A second strut 159 extends longitudinally through the second transverse channel 155 from a proximal end 175 of the middle portion 153 to a distal end 176 of the second end portion 152 to connect the second end portion 152 to the middle portion 153. Thus, the first and second struts 156, 159 maintain the head plate 150 as a unitary structure that is integrally formed as a single unit despite the gaps formed by the first and second transverse channels 154, 155.

During assembly of the oral care implement 100 after the tooth cleaning elements are connected to the unitary head plate 150, the unitary head plate 150 is coupled to the first and second pods 134, 135 so that the first end portion 151 of the head plate 150 forms a portion of the first pod 134 and the second end portion 152 of the head plate 150 forms a portion of the second pod 135. Furthermore, the middle portion 153 of the head plate 150 forms at least a portion of the carrier 160. In certain embodiments, the middle portion 153 of the head plate 150 forms the entirety of the carrier 160. Thus, the first end portion 151 of the head plate 150 is directly connected to the first pod 134 and the second end portion 152 of the head plate 150 is directly connected to the second pod 135. The middle portion 153 is not directly connected to either the first or second pod 134, 135 or any other portion of the base structure 130, but rather the middle portion 153 is movably and/or flexibly supported above the base structure 130 by the first and second pods 134, 135 (and by the first and second end portions 151, 152 of the head plate 150) as has been described above.

The first and second transverse channels 154, 155 are filled with a resilient material 189. The resilient material 189 is omitted from FIG. 7 so that the first and second struts 156, 159 are visible. The resilient connections between the carrier 160 and the first and second pods 134, 135 described above are formed by a combination of the resilient material 189 that fills in the first and second transverse channels 154, 155 and the first and second struts 156, 159. Thus, the middle portion 153 of the head plate 150 is capable of flexing up-and-down and side-to-side relative to the first and second end portions 151, 152. Similarly, when the head plate 150 is coupled to the first and second pods 134, 135, the resilient material 189 and the first and second struts 156, 159 facilitate the movement of the carrier 160 relative to the base structure 130 (and relative to the first and second pods 134, 135) as has been described herein in detail above.

The unitary head plate 150 comprises a plurality of openings 177 extending from a front surface 178 of the head plate 150 to a rear surface 179 of the head plate 150 (only a select few of the openings 177 are labeled in FIG. 7 to avoid clutter). The tooth cleaning elements 105, 106, 163 are positioned within the openings 177 so that a distal end of the tooth cleaning elements 105, 106, 163 protrudes through a rear surface 191 of the head plate 150 and a major portion of the tooth cleaning elements 105, 106, 163 extends from the front surface 192 of the head plate 150. The portions of the tooth cleaning elements 105, 106, 163 that extend from the front surface 192 of the head plate 150 are used to engage the user's teeth and oral surfaces during use of the oral care implement 100.

As discussed above, the tooth cleaning elements 105, 106, 163 are connected to the head plate 150 via an anchor free tufting technique. Thus, the distal ends of the tooth cleaning elements 105 of the first pod 134 are melted together by heat to be anchored in place and to form a first melt mat 193. The distal ends of the tooth cleaning elements 106 of the second pod 135 are similarly melted together by heat to be anchored in place and to form a second melt mat 194. Finally, the distal ends of the tooth cleaning elements 163 of the carrier 160 are melted together by heat to be anchored in place and to form a third melt mat 195.

In the exemplified embodiment, the tooth cleaning elements 105, 106, 163 are illustrated as bristles. Common examples of tooth cleaning elements include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Thus, the tooth cleaning elements may include all bristles, a combination of bristles and elastomeric elements, or all elastomeric elements. Suitable elastomeric materials include any biocompatible resilient material suitable for uses in an oral hygiene apparatus. To provide optimum comfort as well as cleaning benefits, the elastomeric material of any tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

Referring to FIG. 8, an oral care implement 200 in accordance with a second embodiment of the present invention will be described. In the interest of brevity, only components of the oral care implement 200 that are different from the oral care implement 100 will be described herein. Furthermore, similar components will be similarly numbered except that the 200-series of numbers will be used.

The oral care implement 200 generally comprises a handle 210 and a head 220. The handle 210 is generically illustrated and can take on any shape, contour or general appearance as desired. The head 220 is connected to the handle 210, and in certain embodiments may be integrally formed with the handle 210. The head 220 and the handle 210 are formed of a rigid material, such as one of the hard plastic materials discussed herein above.

The head 210 comprises a carrier 260 having a front surface 261 and an opposed rear surface 262. A plurality of tooth cleaning elements 263 extend outwardly from the front surface 261 of the carrier 260. Furthermore, the head 210 comprises a base structure 230 having a front surface 231 and an opposed rear surface 232.

The oral care implement 200 further comprises a first pod 234 extending upwardly from the front surface 231 of the base structure 230 of the head 220. The carrier 260 is movably supported above the front surface 231 of the base structure 230 by the first pod 234. In the exemplified embodiment, the carrier 260 is supported above the front surface 231 of the base structure 230 by the first pod 234 in a cantilevered manner. Due to the support of the carrier 260 by the first pod 234, a gap 265 is formed between the rear surface 262 of the carrier 260 and the front surface 231 of the base structure 230.

Furthermore, in the exemplified embodiment the first pod 234 is merely an upstanding wall that extends upwardly from the front surface 231 of the base structure 230. In this manner, the first pod 234 acts as a living hinge that enables the carrier 260 to flex downwardly into the gap 265 in the direction of the base surface 230 in response to a force (i.e., a brushing force) acting on the carrier 260. The invention is not to be limited to the particular structural arrangement of the first pod 234 in all embodiments and in certain other embodiments the first pod 234 can merely be a hinge, a wall or a protuberance having any shape or configuration that is capable of supporting the carrier 260 in a cantilevered manner as illustrated.

In the exemplified embodiment, the connection between the first pod 234 and the carrier 260 is a rigid connection and the first pod 234 and carrier 260 appear to be integrally formed. However, the invention is not to be so limited and the first pod 234 and carrier 260 can be resiliently connected such that a resilient material extends between the first pod 234 and the carrier 260 to achieve the connection between the first pod 234 and the carrier 260 as has been described above with regard to the oral care implement 100.

The base structure 230 comprises an opening 233 that forms a passageway from the front surface 231 of the base structure 230 to the rear surface 232 of the base structure 230. A mass 280 formed of a resilient material, which may be in the shape of a sphere or otherwise as has been discussed herein above with regard to the mass 180 of the oral care implement 100, is disposed within the opening 233 so that a first portion 281 of the mass 280 protrudes from the front surface 231 of the base structure 230 and a second portion 282 of the mass 280 protrudes from the rear surface 232 of the base structure 230.

The mass 280 is formed of any of the materials that have been described above for the mass 180. Thus, the mass 280 is capable of deformation or displacement in response to a brushing force. Therefore, during brushing, when a normal brushing force is applied to the tooth cleaning elements 263 of the carrier 260, the carrier 260 is translatable toward the front surface 231 of the base structure 230 via the deformation and/or displacement of the mass 280 relative to the base structure 230. Furthermore, because the first portion 281 of the mass 280 that protrudes from the front surface 231 of the base structure 230 is dome-shaped, the carrier 260 can also pivot with respect to the base structure 230 about the first portion 281 of the mass 280 when a normal brushing force is applied to the carrier 260.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care implement comprising:
  a handle;
  a head connected to the handle, the head comprising a base structure having a front surface, a rear surface, an island protruding from the rear surface of the base structure, and a passageway extending through the base structure from the front surface of the base structure to a rear surface of the island;
  a resilient soft tissue cleanser on the rear surface of the base structure, the resilient soft tissue cleanser comprising an aperture through which the island extends;

a mass of a first resilient material positioned within the passageway so that a first portion of the mass protrudes from the front surface of the base structure, the island isolating the resilient soft tissue cleanser from the mass; and a plurality of teeth cleaning elements.

2. The oral care implement according to claim 1 wherein the first portion of the mass comprises a first domed surface and a second portion of the mass comprises a second domed surface.

3. The oral care implement according to claim 2 wherein the mass is a spheroid.

4. The oral care implement according to claim 1 wherein the base structure comprises a basin formed in the rear surface of the base structure, the resilient soft tissue cleanser disposed in the basin, the island comprising an annular wall protruding from a floor of the basin.

5. The oral care implement according to claim 4 wherein the island comprises an outer sidewall surface extending upward from the floor of the basin that is circumferentially surrounded by the resilient soft tissue cleanser.

6. The oral care implement according to claim 1 wherein the resilient soft tissue cleanser is formed of a second resilient material that is different than the first resilient material.

7. The oral care implement according to claim 1 wherein the base structure comprises a distal portion, a proximal portion and a narrowed waist portion between the proximal and distal portions, the passageway located in the narrowed waist portion.

8. The oral care implement according to claim 1 wherein the rear surface of the island is concave.

9. The oral care implement according to claim 1 wherein the passageway has a cross-sectional area that tapers from the rear surface of the island to the front surface of the base structure.

10. The oral care implement according to claim 1 wherein the island is integrally formed with the base structure of a rigid material.

11. The oral care implement according to claim 1 further comprising a first protuberance extending from the base structure, and a carrier having a front surface and a rear surface, the carrier comprising a plurality of teeth cleaning elements extending from the front surface of the carrier, the carrier movably supported above the front surface of the base structure by at least the first protuberance so that a gap exists between the rear surface of the carrier and the front surface of the base structure.

12. The oral care implement according to claim 11 wherein the first portion of the mass contacts the rear surface of the carrier when a force is applied to the plurality of tooth cleaning elements of the carrier in the direction of the front surface of the base structure.

13. The oral care implement according to claim 11, wherein the first protuberance extends from the front surface of the base structure.

14. The oral care implement according to claim 13 further comprising:
a second protuberance extending from the front surface of the base structure; and
the carrier positioned between the first and second protuberances and movably supported above the front surface of the base structure by connections to the first and second protuberances.

15. The oral care implement according to claim 14 wherein the first protuberance is a first pod having a plurality of teeth cleaning elements extending therefrom and the second protuberance is a second pod having a plurality of teeth cleaning elements extending therefrom, the first and second pods being substantially non-movable relative to the base structure.

16. The oral care implement according to claim 13 wherein the carrier is movably supported above the front surface of the base structure in a cantilevered manner by the first protuberance.

17. The oral care implement according to claim 1 wherein a second portion of the mass protrudes from the island.

* * * * *